United States Patent [19]
Gustafson

[11] Patent Number: 5,679,579
[45] Date of Patent: Oct. 21, 1997

[54] IMMUNOFLUORESCENCE MEASUREMENT OF ANALYTES BOUND TO A SUBSTRATE AND APPARATUS THEREFOR

[75] Inventor: Eric Gustafson, Palo Alto, Calif.

[73] Assignee: First Medical, Inc., Mountain View, Calif.

[21] Appl. No.: 592,980

[22] Filed: Jan. 29, 1996

[51] Int. Cl.[6] ................................................. G01N 21/64
[52] U.S. Cl. ..................... 436/172; 436/165; 422/82.08; 250/458.1; 250/459.1
[58] Field of Search ........................... 436/164, 165, 436/172; 422/82.05, 82.08; 250/458.1, 459.1, 461.1, 461.2

[56] References Cited

U.S. PATENT DOCUMENTS

| | | | |
|---|---|---|---|
| Re. 33,581 | 4/1991 | Nicoli et al. | 435/7.2 |
| 3,853,467 | 12/1974 | Giaever | 23/230 |
| 3,926,564 | 12/1975 | Giaever | 23/259 |
| 3,960,451 | 6/1976 | Wirz et al. | 356/161 |
| 3,960,488 | 6/1976 | Giaever | 23/230 |
| 3,960,489 | 6/1976 | Giaever | 23/230 |
| 3,960,490 | 6/1976 | Giaever | 23/230 |
| 3,975,238 | 8/1976 | Bean et al. | 195/103.5 |
| 3,979,184 | 9/1976 | Giaever | 23/253 |
| 3,979,509 | 9/1976 | Giaever | 424/12 |
| 4,011,308 | 3/1977 | Giaever | 424/1.5 |
| 4,018,886 | 4/1977 | Giaever | 424/12 |
| 4,054,646 | 10/1977 | Giaever | 424/12 |
| 4,114,535 | 9/1978 | Giaever | 424/1 |
| 4,172,827 | 10/1979 | Giaever | 260/112 |
| 4,181,501 | 1/1980 | Keese et al. | 23/230 |
| 4,537,861 | 8/1985 | Elings et al. | 436/518 |
| 4,558,012 | 12/1985 | Nygren et al. | 436/501 |
| 4,621,911 | 11/1986 | Lanni et al. | 350/524 |
| 4,647,544 | 3/1987 | Nicoli et al. | 436/518 |
| 4,820,649 | 4/1989 | Kawaguchi et al. | 436/501 |
| 4,876,208 | 10/1989 | Gustafson et al. | 436/531 |
| 4,886,761 | 12/1989 | Gustafson et al. | 436/518 |
| 5,089,387 | 2/1992 | Tsay et al. | 435/6 |
| 5,120,131 | 6/1992 | Lukosz | 356/351 |
| 5,196,350 | 3/1993 | Backman et al. | 436/501 |
| 5,413,939 | 5/1995 | Gustafson et al. | 436/518 |

OTHER PUBLICATIONS

Arwin, H. et al. "A Reflectance Method for Quantification of Immunological Reactions on Surfaces," (1985) *Analytical Biochemistry*, 145:106–112.

Moffatt, A. "Optical Probes May Hasten Shift of Diagnostics from lab to Doc's Office," (1986) *Genetic Engineering News*, p. 18.

Pace, S., "Biosensors and the Clinical Laboratory," (1985) *Medical Instrumentation*, 19(4):168–172.

*Primary Examiner*—Jeffrey Snay
*Attorney, Agent, or Firm*—Townsend and Townsend and Crew LLP

[57] ABSTRACT

A system is disclosed for measuring immunofluorescence of a thin sample layer mounted on a substrate. A sample is located in a radiation beam having a spacially-varying amplitude, for example a series of nodes and antinodes. The sample layer is small to comparison to the period over which the radiation intensity varies, but the support is large in comparison to the period. Thus, when the sample and support are moved relative to the radiation beam, the fluorescence signal from the sample layer will be significantly affected, while the signal from the support is substantially unaffected. The difference between two measurements at different relative orientations of the source and radiation beam can provide a measure of the fluorescence of the sample layer independent of any background scatter of fluorescence of the support. In a preferred embodiment, relative movement between the sample and radiation beam is provided to subject the sample to a time-varying radiation amplitude, and the fluorescence of the sample is obtained from a varying component of the detected signal.

35 Claims, 2 Drawing Sheets

IMMUNOFLUORESCENCE MEASUREMENT OF ANALYTES BOUND TO A SUBSTRATE AND APPARATUS THEREFOR

BACKGROUND OF THE INVENTION

This invention relates to an apparatus and method for measuring the immunofluorescence of a thin sample layer mounted on a substrate.

Many solid-phase immunoassays involve surface illumination and consequent light emissions from molecules attached to the surface. Generally, these emissions travel in all directions. Either these divergent emissions must be collected with expensive and awkward light collection optics to achieve high sensitivity or the inherent inefficiencies and consequent low signal to noise ratio must be accepted.

Many immunoassay systems have been developed using different physically measurable properties of reagents to provide a measurement of an analyte concentration. Radio immunoassay (RIA), immunofluorescence, chemiluminescence, enzyme immunoassays (EIA), free radical immunoassays (FRAT), light scattering nephelometry, transistor bridge probes, indium reflective surfaces, and ultrasonic probes have been applied. These systems use the highly selective reaction between a primary binding reagent material such as an antibody or antigen and an analyte selectively binding therewith.

An attempt by others to develop an optical probe comprising a metal cored diffraction grating coated with a monoclonal antibody specific for a virus, bacterium or other desired antigen has been described by Moffatt, A. GENETIC ENGINEERING NEWS, p. 18, October 1986. The shift in wavelength of reflected light is apparently determined and correlated to a concentration in analyte.

A reflectance method for quantification of immunological reactions on polished crystalline silicon wafer surfaces has been described by Arwin, H. et al., ANALYTICPAL BIOCHEMISTRY, 154:106–112 (1985). Indium surface reflection methods are described by Giaver in U.S. Pat. Nos. 3,853,467, 3,926,564, 3,960,488, 3,960,489, 3,960,490, 3,975,238, 3,979,184, 3,979,509, 4,011,308, 4,018,886, 4,054,646, 4,115,535, 4,172,827 and 4,181,501. Liquid layer thicknesses can be monitored by a reflectance method described in U.S. Pat. No. 3,960,451.

Biosensors such as field effect transistors probes and their use in assays are described by Pace, S., MEDICAL INSTRUMENTATION, (19(4):168–172 (1985). Polysilicon surfaces are included among the possible biosensor surfaces to which primary binding reagents can be attached.

Other patents of interest include U.S. Pat. Nos. 4,537,861; 4,558,012; 4,647,544; 4,820,649; 4,876,208; 4,886,761; 5,089,387; 5,120,131; 5,196,350; and RE 33,581.

U.S. Pat. No. 5,413,939, co-assigned, and having a common inventor, discusses using an interferometer to detect phase shifts due to binding of analyte. In this document, measurements are taken alternately from regions of a disk having immunologically active and inactive portions, to compensate for non-specific binding of analyte to a disk. However, the disclosure is not concerned with measuring immunofluorescence from a thin sample layer.

In immunofluorescence assays, the fluorescence of a dye layer is measured by exciting the dye with light (e.g., having a wavelength of about 600 nm, typically ranging from about 600 nm to 900 nm) which causes the dye to fluoresce. The dye layer is formed as a thin layer (typically of the order of 10 nm, preferably ranging from about 1 nm to 30 nm) on a substrate. Typical dyes are fluorescein, CY5, CY5.5, and the like. The substrate is typically made of plastics material, and may be transparent or translucent, preferably having a thickness of about 1 mm, e.g., typically from 0.5 mm to 3 mm.

The dye layer will usually be formed by immobilizing a plurality of dye molecules on the surface of the substrate as a result of immunological reactors, e.g., conventional immunoassay protocols. Usually, the substrate will have at least one reaction zone defined by a first specific binding substance covalently or non-covalently attached to a defined region on the surface. The substrate will then be reacted one or more times with reaction solutions which result in deposition of the dye molecules within the reaction zone. Most commonly, at least one of the reactions will be with a sample, such as a patient or other biological sample, suspected of containing an analyte, and the amount of dye molecules ultimately bound to the reaction zone will be mediated by the amount of analyte initially present in the sample. A wide variety of particular protocols are described in the patent and scientific literature, including competitive and non-competitive (sandwich) assay, heterogeneous and homogeneous assays, and the like.

There can be inaccuracies in the measurements due to background signals, for example due to Raman scatter or fluorescence of the substrate. Although the signal per unit volume of the substrate is much lower than that of the dye, the substrate is much thicker, so the cumulative background signal can be comparable to the layer from the dye signal at low analyte concentrations.

It would thus be desirable to find a system for measuring fluorescence of the dye layer accurately while minimizing the effects of signals from the substrate.

SUMMARY OF THE INVENTION

The present invention provides an improved binding assay technique. The invention provides a system in which the effects of background radiation and raman scatter from the substrate or support on which a sample layer comprising an antibody or other binding substance, e.g., biotin, with bound dye is mounted can be substantially eliminated, so that measurements more accurately reflect the amount of fluorescence of the sample layer itself.

The invention provides a technique in which light having a spatially varying pattern, e.g., consisting of a series of nodes and anti-nodes is directed at the sample. Because the thickness of the dye in the sample layer is small in comparison to the distance over which the light intensity varies, there will be significant variation in the output from the dye in the sample layer as the relative orientation of the sample and the radiation pattern is altered. On the other hand, the thickness of the substrate on which the sample layer is formed is large in comparison to the distance over which the radiation pattern varies, and since the radiation from the substrate is cumulative, the signal from the substrate will be related to the average value of the radiation intensity throughout the substrate, which will be substantially unaffected by relative movement between the substrate and the radiation pattern.

For example, if the radiation pattern comprises a series of nodes and anti-nodes of light, for example having a wavelength of the order of 500 nm (a helium-neon laser has a wavelength of 632 nm), the dye layer is of the order of 10 nm thick, and the sample substrate is of the order of 1 mm thick, it can be seen that the dye layer is small in comparison to the wavelength of the light, so when the dye layer is located at a node in the radiation pattern, there will be substantially no signal, and when the dye layer is at an antinode, there will be a maximum signal. The substrate, on the other hand, will accommodate thousands of nodes and antinodes, so relative movement between the substrate and the radiation pattern will have little effect on the total amount of radiation passing through the substrate. The substrate is typically at least about a thousand times thicker than the dye layer.

In a broad aspect, the present invention provides a method or apparatus in which a test-piece having a sample layer on a substrate is irradiated with radiation having a spatially varying amplitude pattern, and at least two measurements are taken at different relative orientations of the test-piece and radiation. Preferably, the positions correspond to location of the dye layer in a region of a first determined amplitude, and in a region of a second determined amplitude. More preferably, the first and second determined amplitudes correspond to minimum and maximum amplitudes within the pattern, respectively, or vice versa. One of the amplitudes may be substantially zero, and the other may correspond to the amplitude of the radiation that would be provided directly by a similar light source if the amplitude were not made to vary spatially. Preferably, the ratio of the first and second amplitudes is at least 10:1.

In a preferred development, movement of the test-piece with respect to the radiation pattern is provided, for example, by moving the test-piece or moving or adjusting the radiation source, where the radiation pattern is a stationary pattern (e.g., a standing wave pattern), or by providing a spatially-varying travelling wave pattern, or by any combination of the above, and a series of measurements of fluorescence are taken. The signal due to the dyes in the sample layer can be extracted from the time-varying component of these measurements, for example, by analogue signal processing or more preferably by digitizing the signal and extracting the time varying component thereof. The signal may be averaged over a number of cycles.

If the radiation pattern has a sinusoidally varying amplitude, in a pattern of nodes and anti-nodes, and the sample is moved relative to the radiation pattern in a linear fashion, over several nodes and anti-nodes, the output should be substantially a sinusoidal waveform due to the dye in the sample layer, superimposed on a substantially constant DC offset, due to background signal from the substrate and other parts of the apparatus. If the relative movement is caused by physical movement of the test-piece or of at least a portion of the radiation source, the waveform may be complicated due to non-linearities in the movement. For example, if the test-piece is moved substantially linearly over a number of wavelengths, and periodically reversed, the output will be substantially sinusoidal during the linear movement, with more complicated waveforms adjacent each end of the travel as the test-piece reverses. In such a case, it may be advantageous to digitize the output signal, and compute a value for the fluorescence of the sample from values for the signal corresponding to the substantially linear movement.

In one embodiment, the test-piece can be placed inside a standing-wave laser cavity. This has the advantage that the power circulating in the laser cavity is much higher than the power outside the cavity, but suffers from the drawback that operation of the laser is affected by the test-piece. It is desirable to measure the output signal at a relatively high frequency, preferably at least 1 kHz, to minimize the effects of background noise and physical vibration of the apparatus.

If the test-piece is physically moved, it may be difficult to move the test-piece sufficiently rapidly for high-frequency measurement, as the test-piece may need to be constrained within a holder, increasing the physical size of the apparatus which must be oscillated. Thus it may be preferred to move a mirror forming part of the radiation source. As another example of the radiation source, a Sangac interferometer may be used. This is a well-known instrument, in which light from a laser beam is split into two beams at right angles by a beam splitter, each of which strikes one of two mirrors angled to result in two counter-propagating beams between the mirrors. If at least one of these mirrors is moved, the pattern of nodes and anti-nodes in the region where the beams are superposed will change.

As a further example, the test-piece may be placed in the path of a travelling spatially-varying radiation beam, for example, provided by two superposed beams, which may be of different frequencies.

The precise arrangement used for generating the radiation pattern is unimportant, provided it is capable of providing a pattern by which a signal from the dye in the sample layer can be discriminated from a signal from the substrate. Although this invention is directed to improving detection of immunofluorescence, it will be appreciated by those skilled in the art that the technique may be applied to other fields where it is desired to measure the properties of a thin sample layer on a substrate by means of radiation.

DESCRIPTION OF THE PREFERRED EMBODIMENT

Figure 1:
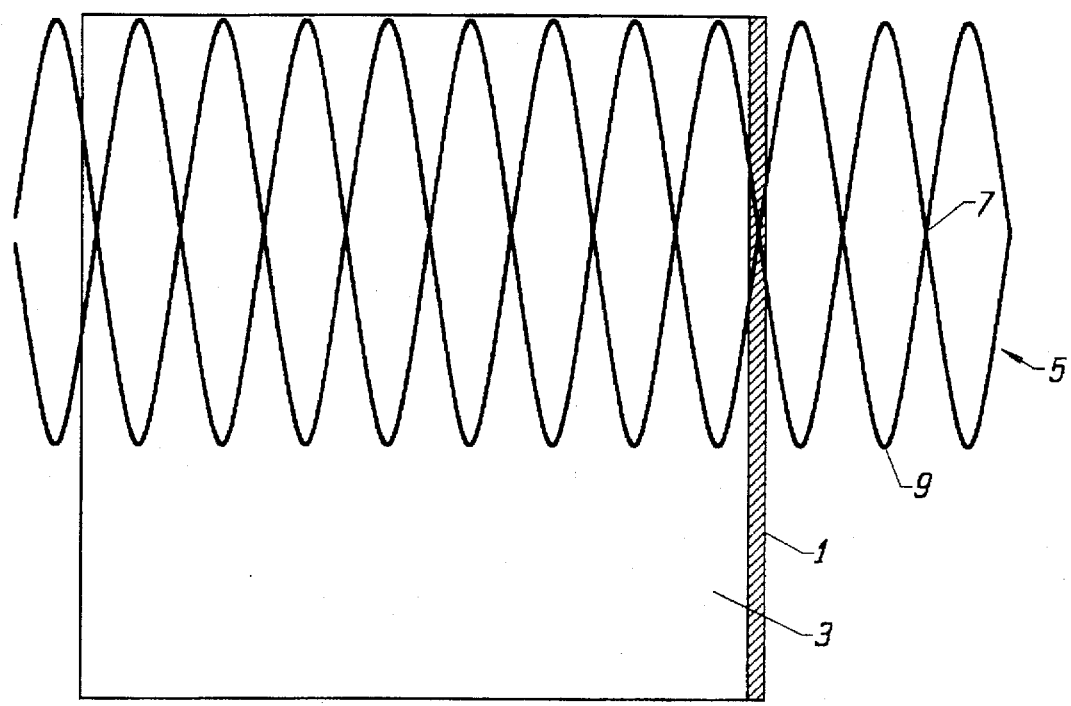
FIG. 1 shows schematically the radiation pattern superimposed on a test-piece with a dye layer at a node in the radiation pattern.

Referring to FIG. 1, a dye layer 1 on a substrate 3 is located in a radiation beam 5 having a plurality of nodes 7 and anti-nodes 9, the dye layer 1 lying at a node 7.

This is a schematic representation, not to scale, and in practice, the thickness of the dye layer would be of the order of 10 nm, the distance between nodes of the order of 300 nm, and the thickness of the substrate of the order of 1 mm, so there would be thousands of nodes and anti-nodes within the substrate 3. Preferably, the dye layer has a thickness no more than about one tenth the distance between adjacent nodes. Note that the drawing represents the envelope of the radiation (i.e., the maximum amplitude), and the actual value of electric field will oscillate at a very high frequency within this envelope. A photodetector will produce an output dependent on the maximum amplitude. The inherent oscillation, typically at a frequency of the order of $10^{14}$ HZ need not be of concern, and should not be construed as related to any references to a time-varying amplitude in this specification.

Since the dye layer 1 is at a node in the signal, there will be substantially no fluorescence from the dye molecules, and the detected radiation will be almost wholly attributable to the background radiation from the substrate.

Figure 2:
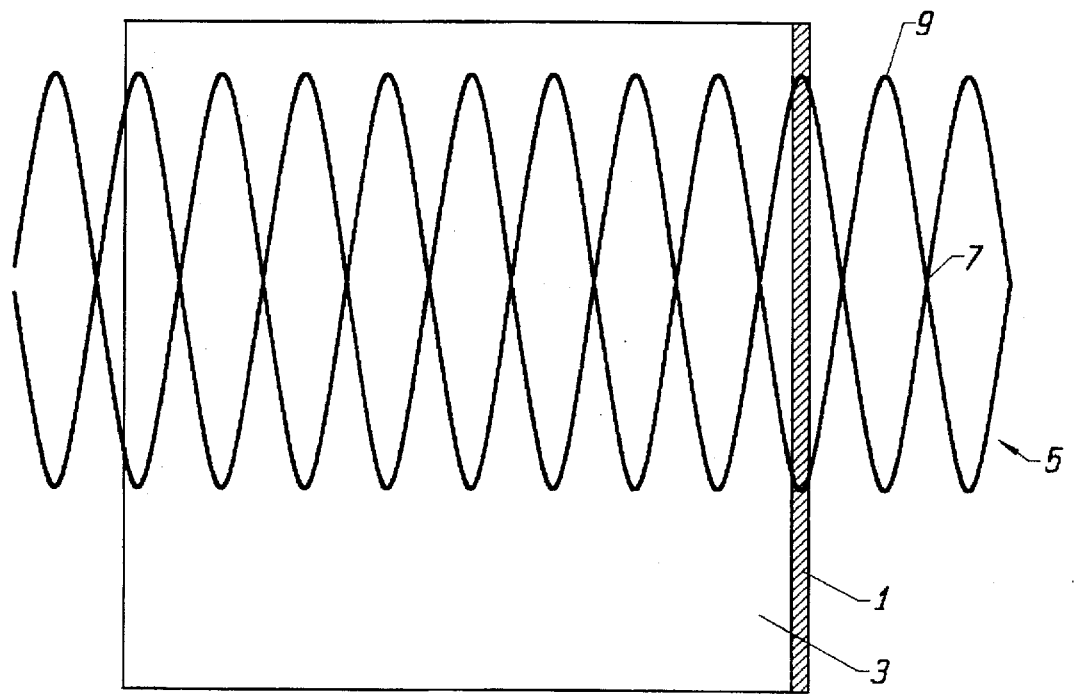
FIG. 2 shows schematically the radiation pattern superimposed on the test-piece with the dye layer at an anti-node in the radiation pattern.

Referring to FIG. 2, the dye layer 1 is located at an anti-node 9 in the radiation pattern, so the fluorescent signal from the dye layer 1 will be a maximum, and will be the same as if the beam were passing through the sample without interference. The signal from the substrate 3 would, however, be virtually unchanged since there will be thousands of nodes and anti-nodes within the support. Preferably, the thickness of the substrate will be at least about 100 times greater than the distance between adjacent nodes, more typically at least about 1000 times greater. The substrate is preferably flat, having substantially parallel planar front and rear faces, on one of which the sample dye layer is provided.

In a simple embodiment, a test-piece comprising a dye layer on a substrate is located in the path of radiation raising a spatially varying amplitude pattern and two measurements of the radiation emitted from the sample are made, preferably with the dye layer located in a radiation pattern as shown in each of FIGS. 1 and 2. The radiation emitted from the dye layer may be filtered to discriminate the light due to fluorescence from background light more clearly. The two measurements are subtracted, to give a measurement of the fluorescence of the dye layer, even when the background signal is of comparable size, or even larger than the signal from the dye layer.

However, taking two static measurements requires careful and precise positioning, for example, at locations of maximum and minimum detected signal and while useful in some applications, the inventor has developed this further to provide an even more effective method of obtaining a value for the fluorescence from the dye layer.

In the preferred method, the radiation pattern is moved rapidly with respect to the dye layer, causing the excitation of the dye to vary with time, while the background signal due to the substrate remains substantially constant. Then, separation of the time varying component, by lock-in detection, spectral analysis, simple analog filtering, or digitizing and calculation, can yield a value for the fluorescence of the dye layer. It is preferred to move the dye layer substantially linearly with respect to the radiation pattern, to produce a sinusoidally varying excitation of the dye molecules. Although the dye layer need only be moved between a single node and adjacent anti-node, it is preferred to move the dye layer over several nodes and anti-nodes, and obtain an average value for the varying component of the signal.

Figure 3:
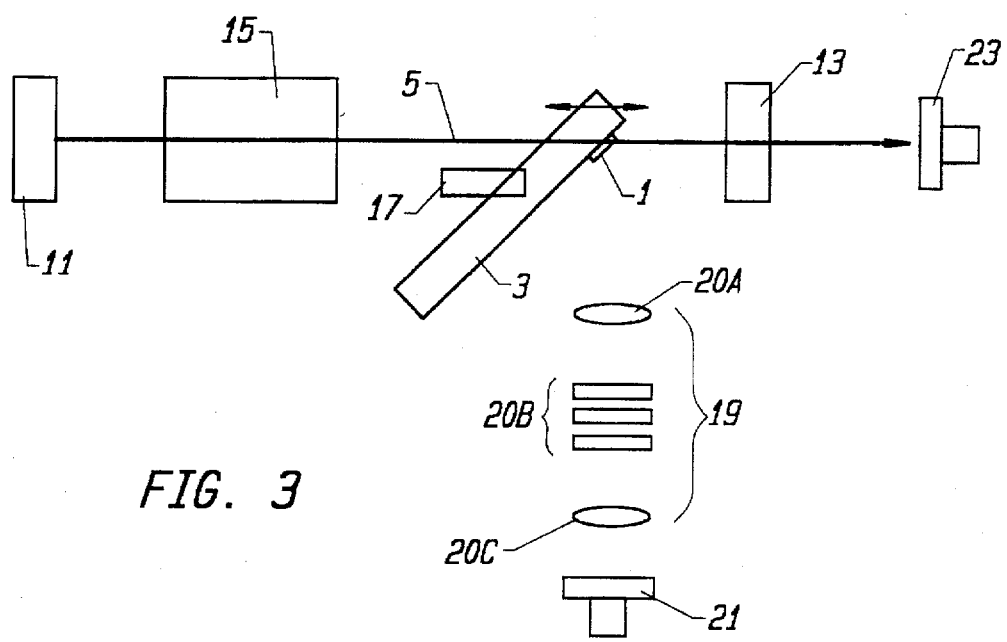
FIG. 3 shows schematically an arrangement in which the test-piece is located in a standing wave laser cavity.

Referring to FIG. 3, one arrangement for locating the sample in a suitable radiation pattern is shown. The substrate 3 on which the dye layer 1 is present is located in a laser cavity 10 comprising a first high reflectance reflector 11, and a partially reflecting output coupler 13, in which cavity a helium neon plasma tube 15 is located. The sample substrate 3 is mounted on a piezoelectric transducer 17, substantially at Brewster's angle with respect to the principal direction of light propagation within the cavity to provide a more predictable pattern of reflected and refracted light from the laser beam, i.e., at Brewster's angle there is no reflection from the substrate. The precise angle is not critical, though it is preferable to avoid normal incidence of the beam and sample, as this may lead to multiple reflections within the cavity, and multi-mode lasing.

Light from the dye layer 1 and support 3 passes through collimator 19. The fluorescent radiation is collected with a lens 20A and the light filtered with narrow band interference filters 20B to separate it from the scattered light. A focusing lens 20C then focuses the fluorescent radiation onto a photodetector 21.

A second photodetector 23 located in the path of light from the output coupler 13 may be provided for normalizing the signal received by detector 21, to compensate for variations in signal strength, for example due to losses in the substrate 3, aging of the laser plasma tube 15, or variations in supply voltage.

An advantage of placing the sample within the cavity is that the power inside the cavity is much greater than the power outside the cavity. This is because the plasma tube 15 typically only has a gain of a few percent so the coupler 13 cannot couple any more power than this outside the cavity, or there is not enough optical feedback, and lasing ceases. Typically a helium neon laser has an output power of between 1 and 10 mW. With a 1% transmission output coupler that means there is about 100 times more power inside the cavity than outside, so between 100 mW and 1 Watt of optical power circulates inside the laser cavity. This optical power excites fluorescence.

Potential disadvantages of this arrangement are that losses in the substrate may affect reliable lasing of the cavity. It is desirable that the substrate is substantially transparent.

The movement of the test-piece is controlled by the signal fed to the piezoelectric transducer, by conventional electronics, which may include a high voltage amplifier, and an analog or digital signal generator to generate the desired drive waveform. It is desirable to oscillate the sample at a relatively high frequency so that the measurement frequency is above several hundred Hz. This reduces the effect of frequency vibrations on the measurement. The detected frequency will be dependent on the rate at which nodes cross the sample layer, and the relationship of this to the driving frequency of the sample can be determined by simple calculation based on the amplitude of vibrations and the wavelength of light used. It may be difficult to oscillate the sample at very high frequencies due to physical constraints, and excess vibration may have adverse effects on the sample or the apparatus.

Suitable transducers include piezoelectric stacks, piezoelectric tubes, magnetostrictive drivers, and the like. The photo detector output is fed to a conventional amplifier and may be fed to conventional analog circuitry for extracting an AC component from the output, which circuitry may be coupled to the drive waveform of the piezoelectric transducer. Alternatively, it may be fed to a digitizer and digital signal processing circuitry. The fluorescence may be calculated according to the well known equations when the thickness of the dye layer is known.

Figure 4:
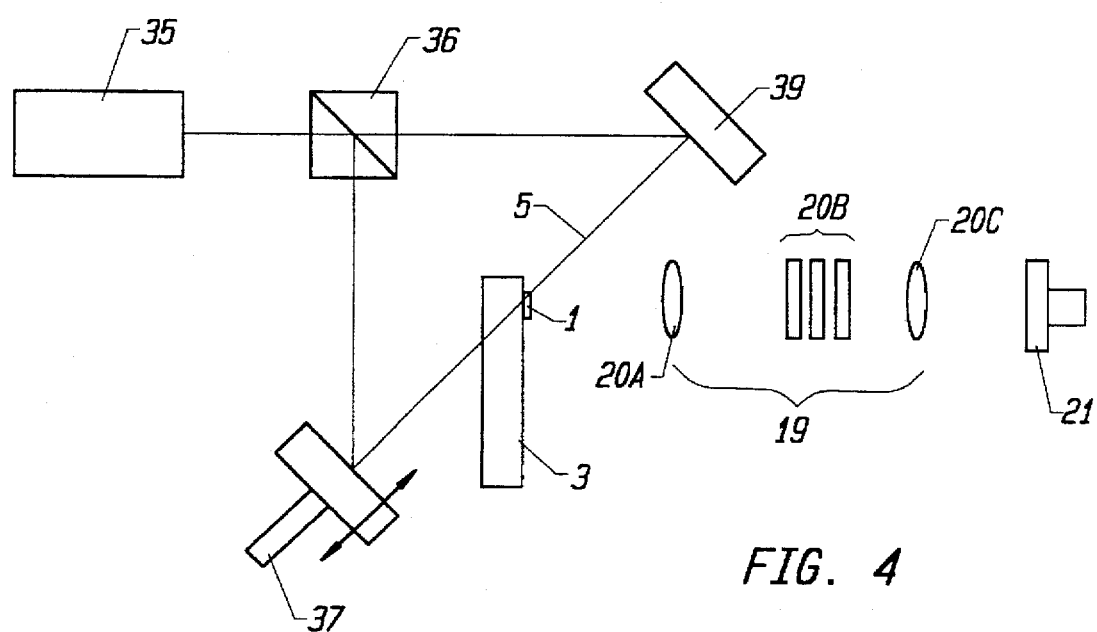
FIG. 4 shows schematically an arrangement in which the test-piece is located in a Sangac interferometer.

Referring to FIG. 4, an alternative arrangement employing a Sangac interferometer is described. The output from a laser 35 passes through a beam splitter 36 to form two perpendicular beams of substantially equal intensity. These two beams strike two mirrors 39, 40 respectively, to produce counter-propagating beams 5 between the two mirrors. The dye layer 1 on the substrate 3 is located at Brewster's angle to the counter-propagating beams 5, for the reasons discussed above, but again, this angle is not critical. The light emitted from the dye in the sample passes through a collimator 19 to a photo detector 21 as described above in relation to the first embodiment. One of the mirrors 40 of the Sangac interferometer is mounted on a piezoelectric transducer 37, movement of which moves the pattern of nodes and anti-nodes in the beam 5. The piezoelectric transducer 37 can be driven by signal generator as discussed above, and the signal from the photodetector 21 detected in a similar way as discussed above for the previous embodiment.

This arrangement has several advantages: All of the light is always injected into the interferometer regardless of the mirror positions. Second, there is no requirement on laser frequency even a multifrequency laser can be used. In addition, the positions of the nodes and antinodes can be shifted back and forth by simply moving one mirror a half wavelength, which may be easier than moving the substrate and dye, particularly at high frequencies. The Sangac interferometer is relatively unaffected by the solid support because it is not an interferometer that resonates the light. Thus, as long as the beams overlap they will produce the required interference pattern.

Other arrangements are possible, for example, a disc of material e.g., glass, having a radiation index greater than air may be moved in the path of one of two counter propagating beams, to produce a varying phase shift. Electro-optic elements which produce a phase shift in dependence on an applied electric field may be used to produce a phase shift.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method of measuring fluorescence of a test-piece comprising a layer of a dye on a substrate, the method comprising;

providing radiation having a first amplitude in a first region, and a second amplitude different from the first amplitude in a second region;

positioning the test-piece relative to the radiation so that said dye layer is in said first region, and making a first measurement indicative of said fluorescence;

positioning the test-piece relative to the radiation so that said dye layer is in said second region, and making a second measurement indicative of said fluorescence;

obtaining a value for said fluorescence from said first and said second measurements, wherein the first and second amplitudes are selected such that the fluorescence emitted by said dye layer only is altered by the relative movement between said test-piece and said radiation.

2. A method according to claim 1, wherein said radiation is provided by a laser.

3. A method according to claim 1, wherein said first amplitude is substantially zero, and wherein said second amplitude is a predetermined amplitude, at least 10 times greater than said first amplitude.

4. A method according to claim 1, wherein said radiation has a plurality of nodes and antinodes, and wherein said first region corresponds to a node, and said second region corresponds to an antinode.

5. A method according to claim 1, wherein obtaining a value for said fluorescence includes subtracting said first measurement from said second measurement.

6. A method according to claim 1, wherein said substrate is at least 1000 times thicker than said dye layer.

7. A method of measuring fluorescence of a test-piece comprising a dye layer on a substrate, comprising;

providing a source of radiation having a plurality of nodes and antinodes;

positioning the dye layer at a node of said radiation and taking a first measurement indicative of said fluorescence;

positioning the dye layer at an antinode of said radiation and taking a second measurement indicative of said fluorescence;

obtaining a value for said fluorescence from said first measurement and said second measurement, wherein the nodes and antinodes are selected such that the fluorescence emitted by said dye layer only is altered by the relative movement between said test-piece and said radiation.

8. A method according to claim 7, wherein said obtaining a value comprises subtracting said first measurement from said second measurement.

9. A method according to claim 7, wherein said substrate is at least 1000 times thicker than said dye layer.

10. A method according to claim 7, wherein said dye layer has a thickness smaller than the distance between adjacent nodes in said radiation.

11. A method according to claim 7, wherein the substrate is at least 100 times thicker than the distance between adjacent nodes in said radiation.

12. A method according to claim 1 or claim 7, wherein said radiation source is provided by interference between two radiation beams.

13. A method according to claim 12, wherein said two beams are counter-propagating beams, providing a standing wave pattern.

14. A method according to claim 1 or claim 7, wherein the position of said sample with respect to the radiation is varied while said fluorescence is being measured.

15. A method according to claim 14, wherein a value for said fluorescence for the sample is determined from a varying component of said measurement.

16. A method according to claim 7, wherein the sample is located within a standing wave laser cavity.

17. A method according to claim 16, wherein the sample is moved reciprocally within said cavity, while said fluorescence is being measured.

18. A method according to claim 7, wherein the sample is located between two mirrors in a Sangac interferometer.

19. A method according to claim 18, wherein one of said mirrors is moved reciprocally while said fluorescence is measured.

20. Apparatus for measuring fluorescence of a layer of a sample on a substrate, the apparatus comprising;

a radiation generator for generating radiation having a first amplitude in a first region, and a second amplitude in a second region;

a positioning member for selectively positioning said sample in said first region and in said second region;

a detector for obtaining measurements indicative of said fluorescence when said sample is irradiated in said first and second regions to obtain at least first and second measurements, respectively, wherein the first and second amplitudes are selected such that the fluorescence emitted by said dye layer only is altered by the relative movement between said test-piece and said radiation.

21. Apparatus according to claim 20, further comprising means for calculating a value for said fluorescence from said first and second measurements.

22. Apparatus according to claim 20, wherein said positioning member is arranged reciprocally to position said sample in said first region and in said second region.

23. Apparatus according to claim 20, wherein said positioning member is arranged to move said substrate and sample.

24. Apparatus according to claim 20, wherein said positioning member is arranged to adjust said radiation source, to move the position of said first and second amplitude regions relative to said sample.

25. Apparatus according to claim 20, wherein the radiation source comprises a standing wave laser cavity, and wherein the sample is positioned within the cavity.

26. Apparatus according to claim 20, wherein said radiation source comprises a Sangac interferometer having two mirrors arranged to produce counter-propagating beams, and wherein the sample is positioned between said two mirrors.

27. A method of measuring fluorescence of a layer of a sample on a substrate, comprising:

providing a source of radiation having a spatially varying amplitude pattern;

positioning the sample in the path of said radiation and subjecting the sample to radiation having a time-varying amplitude, by relative movement between said sample and said amplitude pattern;

measuring a parameter indicative of said fluorescence while said sample is subjected to said radiation having a time-varying amplitude;

obtaining a value for said fluorescence from said parameter, wherein the spatially varying amplitude pattern is selected such that the fluorescence emitted by said dye layer only is altered by the relative movement between said test-piece and said radiation.

28. A method according to claim 27, wherein said value is obtained by analyzing said parameter into static and time-varying components, and extracting said time-varying component.

29. A method according to claim 27, wherein said radiation has a time-varying amplitude corresponding to a determined waveform, and wherein said obtaining a value includes detecting said parameter in synchrony with said determined waveform.

30. A method according to claim 27, wherein said relative movement is provided by moving said substrate and sample relative to said radiation source.

31. A method according to claim 27, wherein said relative movement is provided by adjusting said radiation source to alter said spatially varying pattern.

32. A method according to claim 27, wherein said obtaining a value includes averaging said parameter over time.

33. Apparatus according to claim 20, wherein said positioning member includes a piezoelectric transducer.

34. Apparatus according to claim 20, wherein said positioning member is moved in a time-varying fashion, to subject the sample to radiation having a time-varying amplitude.

35. A method according to claim 1, 7, or 27, wherein the substrate is placed at Brewster's angle with respect to the direction of incident radiation.

* * * * *